United States Patent [19]

Howe et al.

[11] 4,303,439

[45] Dec. 1, 1981

[54] 2-SUBSTITUTED-4-ALKYL OR TRIHALOALKYL-5-OXAZOLECARBOXYLIC ACIDS AS SAFENING AGENTS

[75] Inventors: Robert K. Howe, Bridgeton; Len F. Lee, Maryland Heights, both of Mo.

[73] Assignee: Monsanto Company, St. Louis, Mo.

[21] Appl. No.: 80,747

[22] Filed: Oct. 1, 1979

[51] Int. Cl.³ .................. A01N 43/76; C07D 263/38; C07D 263/34

[52] U.S. Cl. ...................................... 71/88; 548/230; 548/236

[58] Field of Search ............................ 548/230; 71/88

[56] References Cited

U.S. PATENT DOCUMENTS

| | | |
|---|---|---|
| 3,301,832 | 1/1967 | D'Amico . |
| 3,538,110 | 11/1970 | Reif et al. . |
| 3,547,620 | 12/1970 | Olin ........................................ 71/88 |
| 3,574,228 | 4/1971 | Woodley . |
| 4,115,095 | 9/1978 | Franz et al. . |
| 4,137,235 | 1/1979 | Irick et al. . |

OTHER PUBLICATIONS

Kondratleva et al., Zhurnal Obschei Khimii vol. 32, No. 7, pp. 2348-2353 (1962).
Chemische Berrchte Jahrig 86, Nr. 1/1953, pp. 97-108.

*Primary Examiner*—Anton H. Sutto
*Attorney, Agent, or Firm*—Patricia A. Coburn; Donald W. Peterson

[57] ABSTRACT

Derivatives of 2-substituted-4-alkyl or trihaloalkyl-5-oxazolecarboxylic acid have been found to be effective in reducing herbicidal injury to crop plants caused by thiocarbamate and acetanilide herbicides, and especially in reducing herbicidal injury to rice, sorghum or wheat crops, especially rice and sorghum, caused by triallate, alachlor and butachlor herbicides.

11 Claims, No Drawings

2-SUBSTITUTED-4-ALKYL OR TRIHALOALKYL-5-OXAZOLECARBOXYLIC ACIDS AS SAFENING AGENTS

This invention relates to novel derivatives of 2-substituted-4-alkyl or trihaloalkyl-5-oxazolecarboxylic acids as well as their use in compositions and methods for reducing herbicidal injury. More specifically, the invention relates to novel compositions and methods for reducing injury to sorghum, rice and wheat caused by thiocarbamate and acetanilide herbicides as, for example, S-(2,3-dichloroallyl)-diisopropylthiocarbamate, 2-chloro-2',6'-diethyl-N-(methoxymethyl)acetanilide and 2-chloro-2',6'-diethyl-N-(butoxymethyl)acetanilide (hereinafter referred to by their common names as, respectively, triallate, alachor and butachlor) which comprises treating the crop plant locus or the seed of the crop plant with an effective amount of a 2-substituted-4-alkyl or trihaloalkyl-5-oxazolecarboxylic acid or a derivative thereof, which will be described more fully below.

BACKGROUND OF THE INVENTION

Thiocarbamate and acetanilide herbicides, e.g., triallate, alachlor and butachlor are very useful for controlling weeds in the presence of growing crops. Application of these herbicides to crop plants such as rice, sorghum and wheat, at rates necessary to kill or stunt weeds, however, may injure the crop plant, slowing growth and development. Accordingly, the use of these herbicides to control weeds in the presence of rice, sorghum and wheat is rendered less desirable. Obviously, a safening agent consisting of a chemical compound that could be used to treat either the seed of the crop plant, the crop plant locus, or the crop plant itself, such that a reduction of injury due to application of the herbicide without a corresponding reduction of the herbicidal action on the weed, would be quite beneficial.

DESCRIPTION OF THE INVENTION

In accordance with the novel aspects of the present invention, injury to rice, sorghum and wheat due to application thereto of thiocarbamate or acetanilide herbicides, especially triallate, alachlor and butachlor may be reduced, without a corresponding reduction in injury to the weeds, by application to the rice, sorghum or wheat plant locus or the seed of said plants prior to planting, of an effective amount of a safening agent comprising a 2-substituted-4-alkyl or trihaloalkyl-5-oxazolecarboxylic acid, or derivative thereof, having the formula

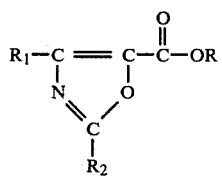

wherein R is hydrogen, lower alkyl, halo (lower) alkyl, or agriculturally acceptable cations; $R_1$ is lower alkyl or polyhalo (lower) alkyl; $R_2$ is hydrogen, lower alkoxy, halogen or phenoxy. The compounds of the above formula are believed to be novel except where $R_2$ is equal to hydrogen.

As used herein, the term "lower alkyl", "lower alkoxy" or, "halo (lower) alkyl" are understood to include alkyl or alkoxy groups having up to five carbon atoms, inclusive.

The term "alkyl" is understood to include branched, unbranched and cyclic alkyl groups.

The term "halo (lower) alkyl" refers to a mono-halo substituted alkyl group containing 1 to 5 carbon atoms as for example, chloromethyl, chloroethyl, bromomethyl, bromoethyl and the like.

The term "polyhalo (lower) alkyl" is employed herein to refer to an alkyl group containing 1 to 5 carbon atoms which is substituted by from three to five halogen atoms, as for example, trifluoromethyl, trichloromethyl, pentafluoroethyl, pentachloroethyl and the like, preferred for use herein is trifluoromethyl.

"Halogen" includes bromine, chlorine, fluorine and iodine atoms.

By the term "agriculturally acceptable cations" is meant those cations that are commonly used to form the salt of the free acid. Such cations include, but are not limited to, alkali metal, alkaline earth, substituted amine and ammonium cations. There are very large numbers of agriculturally acceptable salts suitable for use in this invention as would readily be appreciated by one skilled in the art.

Preferred are those safening agents of the foregoing formula in which R is lower alkyl, especially ethyl, where $R_1$ is methyl or trifluoromethyl and where $R_2$ is chloro, bromo, iodo or ethoxy. Especially preferred are those safening agents of the foregoing formula in which R is ethyl, $R_1$ is methyl and $R_2$ is chloro, bromo or iodo.

The compounds of this invention may be prepared by synthetic methods well known in the oxazole field; see for example French Pat. No. 1,543,853, U.S. Pat. No. 3,538,110, U.S. Pat. No. 4,026,901 and G. Y. Kondrateva and K. Chzhi-Khen, "Synthesis of Some Substituted Oxazoles", ZHURNAL OBSHCHEI KHIMII, Vol. 32, No. 7, pages 2348–2353, July 1962. The examples given below are illustrative of these well-known methods.

EXAMPLE 1

Preparation of Ethyl 4-Methyl-5-Oxazolecarboxylate

This compound was prepared according to the procedure described in French Pat. No. 1,543,853. A mixture of 50.0 g (0.337 moles) of ethyl chloroacetoacetate and 42.0 g (0.933 moles) of formamide was stirred at 120°–135° for 18 hr. Thereafter, the mixture was cooled using an ice bath to 10° C. 300 ml of 1 N $K_2CO_3$ was added dropwise with gas evolution noted. After complete addition of $K_2CO_3$ solution, the reaction mixture was stirred with 200 ml of benzene/ether (2:1) and saturated with NaCl. The insoluble material was filtered and the benzene/ether layer was separated and washed with water, dried ($MgSO_4$) and concentrated under reduced pressure. The brown residue was distilled on a Kugelrohr to give 14.8 g of white solid, mp 31°–33° C.; yield 31%; nmr ($CDCl_3$) 8.0 (s,1H,$C_2$H), 44 (q, J=7 Hz, 2H,$CH_2$), 2.5 (s,3H,$CH_3$), 1.4 (t,3H,$CH_3$).

EXAMPLE 2

Preparation of Ethyl 2-Chloro-4-Methyl-5-Oxazolecarboxylate

To 1.50 g (0.016 mol) of N-isopropylcyclohexylamine in 20 ml of dry THF at −78° C. was added, under nitrogen, 4.1 ml of 2.4 M BuLi in hexane. The solution was stirred at −78° C. for 5 min. A solution of 1.55 g (0.01 mol) of the compound of Example 1, in 10 ml of THF, was added dropwise to the above lithium N-isopropylcyclohexylamide solution. The reaction mixture turned deep red. After 5 min. of stirring, 5 ml of CCl$_4$ was added to the red solution and the reaction mixture was stirred at −78° C. for 1 hr. Thereafter, the reaction mixture was poured into water and extracted with 100 ml of ether. The ether solution was washed with 1 N HCl, dried (MgSO$_4$) and concentrated under reduced pressure. The residue was chromatographed on silica gel using 10% ether/petroleum ether as eluant. The first 800 ml of eluate gave a solid which was recrystallized from hexane at low temperature to give 200 mg of ethyl 2-chloro-4-methyl-5-oxazolecarboxylate as white solid, mp 61°–72° C. An additional 330 mg, mp 55°–58° C., was obtained by concentration of the mother liquor and distillation of the residue; total yield 29%.

Anal. Calculated for C$_7$H$_8$ClNO$_3$: C, 44.34; H, 4.25; N, 7.39; Cl, 18.70. Found: C, 44.29; H, 4.27; N, 4.27; Cl, 18.68.

EXAMPLE 3

Preparation of Ethyl 2-Iodo-4-Methyl-5-Oxazolecarobxylate

To a solution of lithium N-isopropylcyclohexyamide, prepared as described in Example 2 was added at −78° C. a solution of 3.1 g (0.02 mol.) of the compound of Example 1 in 10 ml of THF. The resulting red solution was stirred at −78° C. for 5 min and treated with a solution of 6.34 g (0.025 mol.) of I$_2$ in 15 ml of THF. The resulting light brown solution was stirred for 20 min and poured into a solution of 30 ml of conc. HCl in 200 ml of water. The mixture was extracted with 100 ml of ether. The ether solution was washed with saturated Na$_2$S$_2$O$_3$, dried (MgSO$_4$) and concentrated under reduced pressure. The residue was distilled on a Kugelrohr (0.5 mm Hg) to give 3.29 g of solid which was chromatographed on silica gel with 10% ether/petroleum ether (1:1) as eluant, to give 2.4 g (42%) of crude ethyl 2-iodo-4-methyl-5-oxazolecarboxylate, mp 110°–112° C. Recrystallization of this material from hexane gave pure ethyl 2-iodo-4-methyl-5-oxazolecarboxylate, as white prisms, mp 114°–115° C.

Anal. Calculated for C$_7$H$_8$INO$_3$: C, 29.91; H, 2.88 I, 45.15. Found: C, 29.99; H, 2.93 I, 45.05.

EXAMPLE 4

Preparation of Ethyl 2-Bromo-4-Methyl-5-Oxazolecarboxylate

To a cold (−78° C.) solution of lithium N-isopropylcyclohexylamide was added a solution of 3.1 g (0.02 mol) of the compound of Example 1 in 15 ml of THF. The resulting solution was stirred at −78° C. for 5 min and treated with 3 ml of Br$_2$. The resulting orange solution was stirred for 5 min and poured into 50 ml of 1 N HCl. The mixture was extracted with 150 ml of ether. The ether solution was washed with saturated Na$_2$S$_2$O$_3$, dried (Na$_2$SO$_4$) and concentrated under reduced pressure. The residue was chromatographed on silica gel. The first fraction obtained by eluting with 500 ml of 2% ether/petroleum ether and 500 ml of 5% ether/petroleum ether, yielded 0.2 g of unidentified solid. The second fraction, obtained by eluting with 1 liter of 10% ether/petroleum ether, gave 1.19 g of solid which was recrystallized from hexane, at low temperature, to give 1.0 g (21%) of a 91% (by glc) pure solid, mp 87°–91° C. which was further recrystallized from hexane to give 94% pure ethyl 2-bromo-4-methyl-5-oxazolecarboxylate, mp 94.5°–95.5° C.

Anal. Calculated for C$_7$H$_8$BrNO$_3$: C, 35.92; H, 3.44 N, 5.99; Br, 34.15. Found: C, 35.98; H, 3.45 N, 5.97; Br, 34.15.

EXAMPLE 5

Preparation of Ethyl 2-Chloro-4-Trifluoromethyl-5-Oxazolecarboxylate

A magnetically stirred mixture of ethyl 2-chloro-4,4,4-trifluoroacetoacetate (21.9 g, 0.1 mol) and sec-butyl carbamate (35.1 g, 0.3 mol) was heated with an oil bath at 150°±5° C. overnight. After cooling to ambient temperature, the mixture was slurried in ether. The ether slurry was washed three times with water and the ether layer was then extracted with 75 ml of saturated NaHCO$_3$ solution. The yellow aqueous phase was washed with ether and then cautiously acidified with concentrated HCl. The oily suspension was extracted with ether, which was dried over MgSO$_4$, and concentrated in vacuo to yield 10.0 g of yellow oil. NMR spectrum indicated that this was approximately a 4:1 mixture of ethyl and sec-butyl esters. Sodium (1.18 g, 49 mmol) was added to 500 ml of absolute ethanol and this sodium ethoxide solution was treated in one portion with a solution of the 4:1 mixture of esters in 100 ml of absolute ethanol. This yellow solution was stirred overnight at ambient temperatures under a CaSO$_4$ drying tube. This mixture was next neutralized with concentrated HCl and the whole mixture was concentrated in vacuo. The resulting solid was partitioned between ether and 5% HCl. The dried (MgSO$_4$) ether layer was concentrated in vacuo to yield a yellow glass. Flash distillation at 80 C/1.5 mm yielded a small amount of starting sec-butyl carbamate which was carried through the workup. At 130 C/1,5 mm, Kugelrohr distillation yielded 5-carboethoxy-4-(trifluoromethyl)-2-oxazolinone as a pale yellow glass which solidified upon standing; 8.3 g (41%); mp 50°–53° C.

Anal. Calculated for C$_7$H$_6$F$_3$NO$_4$: C, 37.35; H, 2.69; N, 6.22. Found: C, 37.45; H, 2.63; N, 6.32.

To 2.25 g (10.0 mol) of the oxazolinone in 3.5 ml of POCl$_3$ was added dropwise at 0° C. 1.2 ml (11.0 mol) of 2,6-lutidine. The resulting light brown mixture was heated at reflux for 2 hours and excess POCl$_3$ removed in vacuo. The residual brown oil was dissolved in CH$_2$Cl$_2$, washed with water and thereafter concentrated in vacuo to yield a brown oil; 2.45 g. Bulb to bulb distillation at 60–80 C/0.5 mm yielded ethyl-2-chloro-4-trifluoromethyl-5-oxazolecarboxylate as a colorless oil; 1.9 g (78%).

Anal. Calculated for C$_7$H$_5$ClF$_3$NO$_3$: C, 34.52; H, 2.07; Cl, 14.56; N, 5.75. Found: C, 34.58; H, 2.08; Cl, 14.56; N, 5.87.

EXAMPLE 6

Preparation of Ethyl 2-Ethoxy-4-Trifluoromethyl-5-Oxazolecarboxylate

The compound of Example 5, ethyl 2-chloro-4-trifluoromethyl-5-oxazolecarboxylate (3.2 g; 0.013 mol) was added to NaOEt. The reaction was allowed to proceed at room temperature for 98 hours. Gas chromatographic analysis at this point determined the completion of the reaction. The light yellow liquid was then slurried in ether, washed with NaOH (5%), dried (MgSO$_4$) and concentrated in vacuo to give 2.8 g of a brown semi-solid. Bulb to bulb distillation at 125° C./0.25 mm gave 1.93 g of ethyl 2-ethoxy-4-trifluoromethyl-5-oxazolecarboxylate as a colorless oil; bp 125° C., yield 59%.

Anal. Calculated for $C_9H_{10}F_3NO_4$: C, 42.70; H, 3.98; N, 5.53. Found: C, 42.58; H, 3.97; N, 5.48.

EXAMPLE 7

Preparation of Ethyl 2-Phenoxy-4-Trifluoromethyl-5-Oxazolecarboxylate

The compound of Example 5, ethyl 2-chloro-4-trifluoromethyl-5-oxazolecarboxylate (4.87 g; 0.02 mol) was added to a mixture of sodium phenol in 100 ml DMF. The reaction was allowed to progress at ambient temperature for 1 hour. Gas chromatographic analysis, at this point, indicated the completion of the reaction. The dark brown liquid was then slurried in ether and washed 5 times with NaOH (5%) and $H_2O$. The resulting brown liquid was dried ($MgSO_4$) and concentrated in vacuo to yield 5.2 g of a brown semi-solid. Bulb to bulb distillation at 75° C./25 mm gave 1.7 g of a colorless oil. Further distillation at 130° C./0.25 mm gave 2.8 g of a white solid. Recrystallization from methylcyclohexane gave 1.08 g of pure white solid, ethyl 2-phenoxy-4-trifluoromethyl-5-oxazolecarboxylate, mp 75°–77° C., yield 18%.

Anal. Calculated for $C_{13}H_{10}F_3NO_4$: C, 51.84; H, 3.35; N, 4.65. Found: C, 51.98; H, 3.38; N, 4.67.

In accordance with the novel aspects of the present invention, the 2-substituted-4-alkyl or 4-trihaloalkyl-5-oxazolecarboxylates are useful for reducing herbicidal injury to crop plants, such as rice, sorghum and wheat, caused by thiocarbamate and acetamide herbicides, as for example, triallate, alachlor and butachlor. The compounds of the present invention are preferentially employed as safeners for triallate herbicide in sorghum and rice, more preferably for triallate herbicide in sorghum. The compounds of the present invention are also particularly effective as safeners for alachlor herbicide in rice and sorghum and especially for sorghum.

The amount of safening agent employed in the methods and compositions of the invention will vary depending upon the manner of application, rate of application, environmental factors, as well as other factors known in the art. In each instance, the amount employed is a "safening effective amount", i.e., the amount which reduces crop injury by the herbicide.

The safening agent may be applied to the plant locus in a mixture with the herbicide or it may be applied directly to the crop seed itself. By application to the "plant locus" is meant application to the plant growing medium, such as the soil, as well as the seeds, emerging seedlings, roots, stems, leaves, flowers, fruits or other plant parts.

To illustrate the effectiveness of the 2-substituted-4-alkyl or 4-trihaloalkyl-5-oxazolecarboxylates of this invention the following examples are presented. These examples are presented merely as being illustrative of the novel aspects of the invention and are not intended to be a limitation as to the scope thereof.

EXAMPLE 8

A good grade of top soil is placed in a container and compacted to a depth of approximately 1.27 cm. from the top of said container. A predetermined number of seeds, of the crop to be tested, are placed on top of the soil. A quantity of soil sufficient to substantially fill the container is measured and placed in a second container. A measured quantity of the safening agent dispersed or dissolved in a suitable carrier is applied to the soil in the second container. A measured quantity of herbicide dispersed or dissolved in a suitable carrier is then sprayed on the soil already treated with the safening agent. The soil containing the safening agent and the herbicide is thoroughly mixed. This mixing is sometimes referred to as incorporation of the herbicide and safening agent into the soil. The mixing or incorporation provides a substantially uniform distribution of the safening agent and herbicide throughout the soil. The crop seeds are covered with the soil containing the safening agent and herbicide and the pans are leveled. The pans are then placed on a sand bench in the greenhouse and watered from below as needed. The crop plants are observed at the end of approximately 21 days and the results in terms of percent inhibition of each seed lot are recorded. For each test series a pan of plants is also prepared containing no herbicide and no safening agent as a control. For each series of tests the herbicidal effect of the herbicide is observed from pans of crop plants treated with the same quantity of herbicide alone.

The "safening effect" is determined by adding the herbicidal effect, i.e., % inhibition, of the herbicide when applied alone to the herbicidal effect, i.e. % inhibition, of the safening agent when applied alone (in no instance, however, will this sum be greater than 100) and subtracting from that, the combined herbicidal effect, i.e. % inhibition, when the herbicide and safening agent are incorporated into the soil as discussed above.

Table I summarizes the results obtained when several of the compounds of the present invention were tested in accordance with the procedure of Example 8.

TABLE I

| Herbicide | Rate of Herb. (kg/h) | Safening Agent Compound of Example | Rate of Safening Agent (kg/h) | Safening Effect* Crop |||
|---|---|---|---|---|---|---|
| | | | | Rice | Sorghum | Wheat |
| Triallate | 0.56 | 1 | 8.96 | * | 40 | * |
| Alachlor | 2.24 | 1 | 8.96 | * | * | * |
| Butachlor | 4.48 | 1 | 8.96 | * | 20 | * |
| Triallate | 0.56 | 3 | 8.96 | 60 | 60 | 20 |
| Alachlor | 4.48 | 3 | 8.96 | * | 29 | * |
| Butachlor | 4.48 | 3 | 8.96 | 33 | 58 | 28 |
| Triallate | 0.56 | 2 | 8.96 | 23 | 75 | * |
| Alachlor | 2.24 | 2 | 8.96 | 20 | * | * |
| Butachlor | 4.48 | 2 | 8.96 | 60 | * | * |
| Triallate | 0.56 | 4 | 8.96 | 40 | 80 | * |
| Alachlor | 2.24 | 4 | 8.96 | 25 | 23 | * |
| Butachlor | 4.48 | 4 | 8.96 | 63 | * | * |
| Triallate | 0.56 | 5 | 8.96 | * | * | * |
| Alachlor | 2.24 | 5 | 8.96 | * | * | * |
| Butachlor | 6.72 | 5 | 8.96 | 50 | * | * |

TABLE I-continued

| Herbicide | Rate of Herb. (kg/h) | Safening Agent Compound of Example | Rate of Safening Agent (kg/h) | Safening Effect* Crop | | |
|---|---|---|---|---|---|---|
| | | | | Rice | Sorghum | Wheat |
| Triallate | 0.56 | 7 | 8.96 | * | 57 | * |
| Alachlor | 2.24 | 7 | 8.96 | * | * | 30 |
| Butachlor | 6.72 | 7 | 8.96 | * | * | * |
| Triallate | 0.56 | 6 | 8.96 | * | 80 | * |
| Alachlor | 2.24 | 6 | 8.96 | * | 45 | * |
| Butachlor | 6.72 | 6 | 8.96 | * | 45 | 60 |

*Safening effect observed between 0 and 19.

In accordance with the procedure described in Example 8, the compounds of Example 3 and 4 were tested utilizing alachlor herbicide at varying rates. The results observed are summarized in Table II.

TABLE II

| Rate of Alachlor kg/h | Safening Agent Compound of Example | Rate of Safening Agent kg/h | Safening Effect* Crop | | |
|---|---|---|---|---|---|
| | | | Rice | Sorghum | Wheat |
| 0.56 | 4 | 8.96 | 30 | 30 | 20 |
| 1.12 | 4 | 8.96 | 25 | 32 | 32 |
| 2.24 | 4 | 8.96 | 25 | 35 | 20 |
| 4.42 | 4 | 8.96 | * | * | * |
| 0.56 | 3 | 8.96 | 90 | * | 25 |
| 1.12 | 3 | 8.96 | 90 | * | 20 |
| 2.24 | 3 | 8.96 | 20 | * | * |
| 4.48 | 3 | 8.96 | * | * | * |

*Safening effect observed between 0 and 19.

EXAMPLE 9

Plastic pots (4×4×3 inches deep) were filled with 2 inches of Ray silt loam soil. The compound of Example 2 and butachlor herbicide were applied sequentially to the soil surface with a belt sprayer. Pre-soaked rice (2 day duration) was seeded into flooded pots. The water level was lowered to the soil surface after 24 hours and maintained at this level for 5 or 6 days after which the pots were reflooded for the duration of the test. Pots containing rice plants to which butachlor alone was applied served as the control. The results are summarized in Table III.

TABLE III

| Control - No Safening Agent | | | Test | | | |
|---|---|---|---|---|---|---|
| Rate of Butachlor (kg/h) | Rate of Safening Agent (kg/h) | % Inhibition | Rate of Butachlor (kg/h) | Rate of Safening Agent (kg/h) | % Inhibition | Safening Effect* |
| | | | 0 | 0.56 | 0 | — |
| 0.07 | 0 | 59 | 0.07 | 0.56 | 13 | 46 |
| 0.28 | 0 | 95 | 0.28 | 0.56 | 18 | 77 |
| 1.12 | 0 | 100 | 1.12 | 0.56 | 96 | * |

*Safening effect observed between 0 and 19.

The compound of Example 4 did not safen sorghum plants against the herbicidal effects of alachlor herbicide when applied to the sorghum seed, prior to planting, at rates varying from 0.031 to 1 gram of compound per kilogram of sorghum seed. Alachlor herbicide was applied to the soil surface at rates of 0.28 to 4.48 kilograms per hectare utilizing a belt sprayer.

The above examples illustrate that the compounds of the present invention are useful in reducing herbicidal injury to various crop plants. The preferred crop plants to be safened by the compounds of the invention are sorghum, rice and wheat, especially preferred are sorghum and rice. The compounds of the invention effectively safen thiocarbamate and acetanilide herbicides, preferably triallate, alachlor and butachlor herbicides.

Compounds of this invention wherein R is lower alkyl, especially ethyl, $R_1$ is methyl or trifluoromethyl and wherein $R_2$ is iodo, bromo or ethoxy are particularly useful to safen sorghum against the herbicidal effects of triallate, alachlor or butachlor.

Compounds of this invention wherein R is lower alkyl, especially ethyl, $R_1$ is methyl and $R_2$ is chloro or bromo are particularly useful to safen rice against the herbicidal effects of triallate, alachlor or butachlor herbicides. The safening agents may be applied to the plant locus as a mixture, i.e., a mixture of a herbicidally effective amount of triallate, alachlor or butachlor and a safening effective amount of safening agent, or sequentially, i.e., the plant locus may be treated with an effective amount of triallate, alachlor or butachlor followed by a treatment with the safening agent or vice versa. The ratio of herbicide to safening agent may vary depending upon various factors, such as the weeds to be inhibited, mode of application, etc., but normally a herbicide to safening agent ratio ranging from 1:25 to 25:1, preferably 1:15 to 15:1, and most preferably 1:10 to 10:1 parts by weight may be employed.

The herbicide, safening agent or mixture thereof may be applied to the plant locus alone or the herbicide, safening agent or mixture thereof may be applied in conjunction with a material referred to in the art as an adjuvant in liquid or solid form. Mixtures containing the appropriate herbicide and safening agent usually are prepared by admixing said herbicide and safening agent with an adjuvant including diluents, extenders, carriers and conditioning agents to provide compositions in the form of finely-divided particulate solids, granules, pellets, wettable powders, dusts, solutions and aqueous dispersions or emulsions. Thus, the mixture may include an adjuvant such as a finely-divided particulate solid, a solvent liquid of organic origin, water, a wetting agent, dispersing agent, or emulsifying agent or any suitable combination of these.

When applying the herbicide, safening agent or mixtures thereof to the plant locus, useful finely-divided solid carriers and extenders include, for example, the talcs, clays, pumice, silica, diatomaceous earth, quartz, Fullers earth, sulfur, powdered cork, powdered wood, walnut flour, chalk, tobacco dust, charcoal and the like. Typical liquid diluents useful include for example, Stoddard solvent, acetone, alcohols, glycols, ethyl acetate, benzene and the like. Such compositions, particularly liquids and wettable powders, usually contain as a conditioning agent one or more surface-active agents in amounts sufficient to render a given composition readily dispersible in water or in oil. By the term "surface-active agent", it is understood that wetting agents, dispersing agents, suspending agents and emulsifying agents are included therein. Such surface-active agents are well known and reference is made to U.S. Pat. No. 2,547,724, Columns 3 and 4, for detailed examples of the same.

Compositions of this invention generally contain from about 5 to 95 parts herbicide and safening agent, about 1 to 50 parts surface-active agent and about 4 to 94 parts solvent, all parts being by weight based on the total weight of the composition.

The application of the herbicide, safening agent or mixtures thereof in a liquid or particulate solid form can be carried out by conventional techniques utilizing, for example, spreaders, power dusters, boom and hand sprayers, spray dusters and granular applicators. The compositions can also be applied from airplanes as a dust or spray. If desired, application of the compositions of the invention to plants can be accomplished by incorporating the compositions in the soil or other media.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A method of reducing injury to rice plants due to application thereto of butachlor herbicide which comprises applying to the plant locus a safening effective amount of a compound having the formula

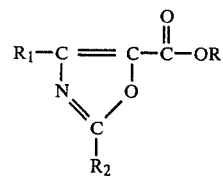

wherein R is hydrogen, alkyl containing 1 to 5 carbon atoms or agriculturally acceptable cations; $R_1$ is alkyl containing 1 to 5 carbon atoms or trifluoromethyl; $R_2$ is halogen.

2. A method according to claim 1 wherein R is alkyl containing 1 to 5 carbon atoms, $R_1$ is methyl and $R_2$ is iodo or bromo.

3. A method according to claim 1 wherein R is alkyl containing 1-5 carbon atoms, $R_1$ is methyl or trifluoromethyl.

4. A method according to claim 1 wherein R is ethyl, $R_1$ is methyl or trifluoromethyl and $R_2$ is halo.

5. A method according to claim 1 wherein said compound is ethyl 2-bromo-4-methyl-5-oxazolecarboxylate.

6. A mixture which comprises a herbicidally effective amount of butachlor herbicide and a safening effective amount of a compound having the formula

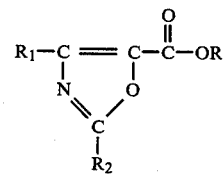

wherein R is hydrogen, alkyl containing 1 to 5 carbon atoms or agriculturally acceptable cations; $R_1$ is alkyl containing 1 to 5 carbon atoms or trifluoromethyl; $R_2$ is halogen.

7. A mixture according to claim 6 wherein R is alkyl containing 1 to 5 carbon atoms, $R_1$ is methyl and $R_2$ is iodo or bromo.

8. A mixture according to claim 6 wherein R is alkyl containing 1 to 5 carbon atoms, $R_1$ is methyl or trifluoromethyl.

9. A mixture according to claim 6 wherein the ratio of butachlor herbicide to safening agent is from 1:25 parts by weight to about 25:1 parts by weight.

10. A mixture according to claim 6 wherein R is ethyl, $R_1$ is methyl or trifluoromethyl and $R_2$ is halo.

11. A mixture according to claim 6 wherein said compound is ethyl 2-bromo-4-methyl-5-oxazolecarboxylate.

* * * * *